United States Patent [19]
Goldberg et al.

[11] Patent Number: 5,242,949
[45] Date of Patent: Sep. 7, 1993

[54] TREATING CLASSIC MIGRAINE

[75] Inventors: Arthur H. Goldberg, Montclair, N.J.; Leonard Lachman, Fort Salonga, N.Y.

[73] Assignee: Rugby-Darby Group Companies, Inc., Rockville Centre, N.Y.

[21] Appl. No.: 850,566

[22] Filed: Mar. 13, 1992

[51] Int. Cl.$^5$ ............... A61K 31/135; A61K 31/535; A61K 31/405; A61K 31/22
[52] U.S. Cl. .................. 514/652; 514/236.2; 514/415; 514/546; 514/944; 514/969
[58] Field of Search ............. 514/236.2, 415, 546, 514/620, 652, 944, 969

[56] References Cited

U.S. PATENT DOCUMENTS 4,394,390  7/1983  Hussain et al. ............... 514/652
4,428,883  1/1984  Hussain ....................... 514/652

Primary Examiner—Frederick E. Waddell
Assistant Examiner—K. Weddington

[57] ABSTRACT

This invention relates to a method for treating classical migraine headaches. Pursuant to this method, a therapeutic amount of β-adrenergic-blocking agent is administered to a person suffering a migraine attack promptly upon onset of aura. The invention further relates to a method wherein the blocking agent is nasally administered.

17 Claims, 5 Drawing Sheets

TREATING CLASSIC MIGRAINE

BACKGROUND OF THE INVENTION

1. Field of Invention

The present invention relates to a novel method for treatment of a classical migraine attack. A β-adrenergic-blocking agent is administered to a person promptly upon onset of aura. The therapeutic dose is desirably provided by nasal administration.

2. Description of the Prior Art

Migraine is a common syndrome characterized by recurrent paroxysmal attacks of headache, often throbbing in character and sometimes, but not invariably, unilateral in distribution. The attacks often last for hours, less commonly for several days. This headache is severe and may be quite incapacitating. Its pain is frequency accompanied by photophobia, nausea, vomiting, and prostration.

β-adrenergic-blocking agents are well known for the prophylaxis of migraine. However, these blocking agents have not generally been shown to be effective in the management of the symptoms of an acute migraine attack. Once the attack has commenced, it has been widely reported that it is too late to administer these blocking agents. In this circumstance, a treatment of choice becomes a drug such as an ergotamine.

As a result of the foregoing, a normal procedure for individuals subject to migraines involves the daily administration of a prophylactic dosage of a β-adrenergic-blocking agent such as propranolol. This essentially involves maintaining a therapeutic level or concentration of blocking agent in a person's bloodstream on a long term basis which may be months in duration.

That procedure has been shown to be effective in reducing the frequency and severity of migraine attacks in humans. A drawback, however, is the requirement for virtually constant drug therapy. Various adverse reactions to β-adrenergic-blocking agents are known. In particular, at the high level of dosage utilized for prophylaxis, there are possibilities of side effects such as bradycardia, hypotension and dizziness. Further, abrupt discontinuance of the drug has still other potential effects including the precipitation of exacerbation of angina, myocardial infarction and ventricular dysrhythmias.

Another drawback of that procedure involves individuals having certain medical complications. For example, those who are pregnant, suffering hepatic impairment or having bronchitis or emphysema can be subjected to its long term, virtually constant drug exposure only under closely monitored conditions, if at all. Consequently, many prospective patients are precluded from the benefits of that procedure.

SUMMARY OF THE INVENTION

In view of the foregoing, it is apparent that a serious need exists for an improved method for utilizing β-adrenergic-blocking agents for the control of migraine. Thus, it is an object of the present invention to devise a method whereby the need for chronic administration of the blocking agents can be avoided. A further object of this invention involves the reduction in total dosage amount, so as to minimize the adverse reactions to this drug therapy.

It has been discovered that the foregoing objectives may be achieved in the treatment of certain migraines through the selective and acute administration of β-adrenergic-blocking agents. More specifically, a blocking agent is provided to a person in therapeutically effective amount promptly after the time of onset of aura.

It has been discovered that the β-adrenergic-blocking agent is desirably provided in a composition suitable for nasal administration. This ensures prompt and efficient delivery of the blocking agent to the sites governing migraine attack within the time constraint for effective use.

It has further been discovered that, upon administration as aforesaid, β-adrenergic-blocking agents function in more than a prophylactic manner. In accordance with the method of the present invention, these blocking agents successfully treat and may even abort classical migraine headaches.

DETAILED DESCRIPTION OF THE INVENTION

Figure 1:
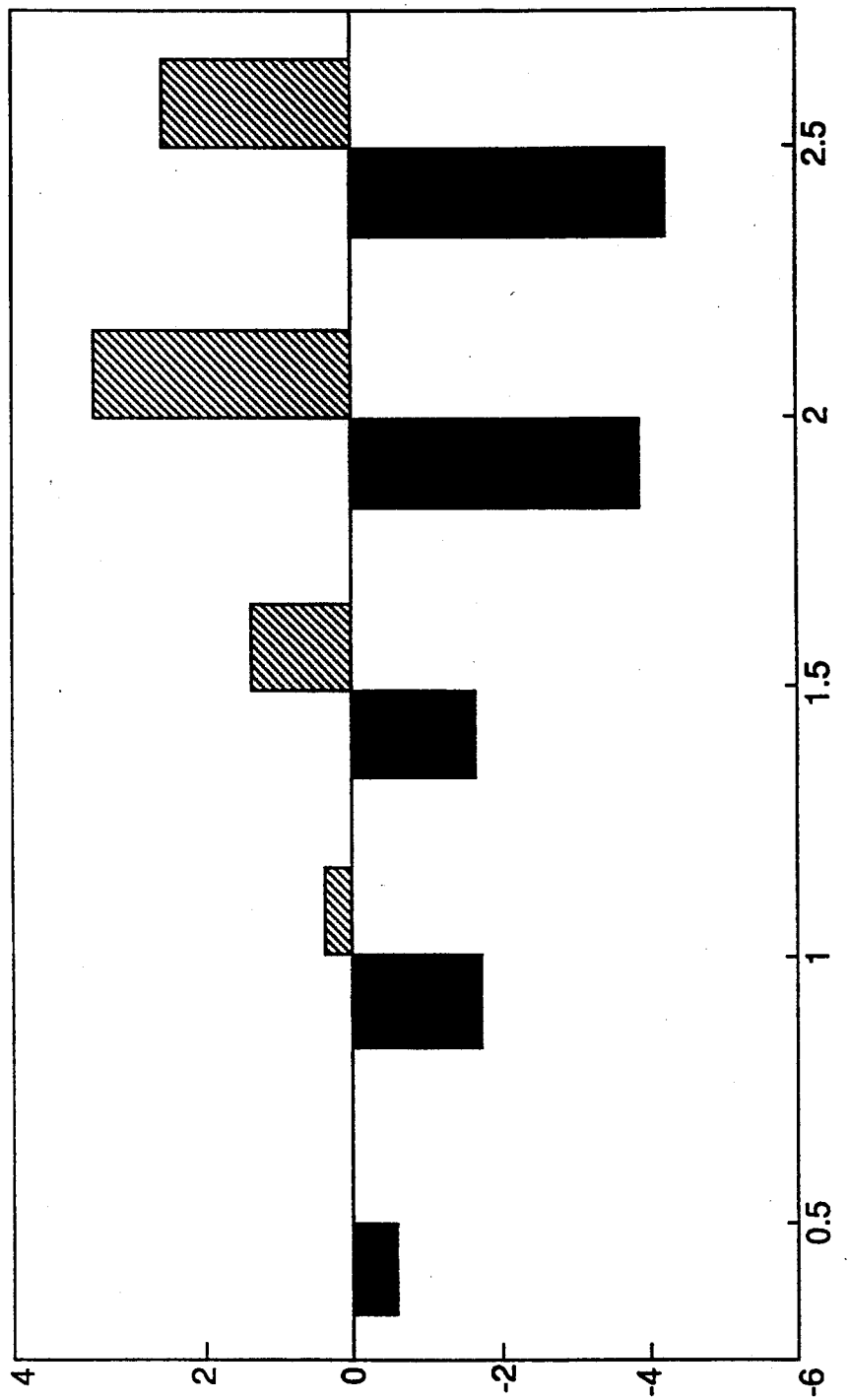
FIG. 1 is a graphic depiction of the comparative results on nausea experienced by individuals having migraines treated with β-adrenergic-blocking agent as opposed to placebo.

Individuals suffering a classic migraine attack experience some warning of impending pain. This prodrome or "aura" can take various forms, but most often involves visual or sensory phenomena (loss of part of the field of vision, bright or colored lights and geometric patterns, the so-called "fortification spectrum", or tinglings and pins and needles in the lips or hands). In other instances, the warning may be virtually subliminal; a person simply becomes aware that an attack is in progress before symptoms develop. The aura of a migraine normally starts between 15 and 60 minutes prior to the commencement of such symptoms as pain.

According to the present invention, it has been discovered that a β-adrenergic-blocking agent is effective for treatment of migraine when administered promptly after onset of aura. If the blocking agent is biologically available during the beginning of a classical migraine attack, it can effectively treat the attendant pain and/or other adverse symptoms.

It is desirable that administration of the β-adrenergic-blocking agent occur as soon as possible during a migraine attack. As symptoms persist and/or become more severe during an attack, they become less amenable to treatment. Consequently, it is desirable to commence administration before the migraine fully develops and especially within 30, more desirably 10, minutes of onset of aura.

In contrast to the prior art procedure involving frequent, purely prophylactic dosages of blocking agent, the present invention involves a targeted administration. The drug is administered acutely, only when there is an indication that a migraine attack has commenced. This permits a far more direct and less intrusive use of β-adrenergic-blocking agents. They may be administered only as needed and in reduced dosage amount as compared to a prophylactic procedure. As a consequence, occurrences of adverse drug reaction, overdosage and/or discontinuance reaction are markedly reduced. This increases the availability of this form of therapy for many classes of individuals suffering from migraine.

In accordance with the present invention, the dosage requirements for β-adrenergic-blocking agents are greatly reduced. In the prior art, it was customary to provide sufficient blocking agent to maintain an effective concentration in the blood stream over an extended time. Doses would be administered chronically, each day for weeks or even months. The present invention, on the other hand, requires an effective blood concentration for a much shorter time period. Administration is specific to a migraine attack which has already started and the drug is intended to function immediately. Consequently, far less blocking agent is required.

For example, pursuant to the prior art procedures of prophylactic doses of β-adrenergic-blocking agent, it is customary to administer no less than about 80 mg, and up to about 240 mg, of propanolol hydrochloride per day. For the targeted method of the present invention, however, the preferred dose is normally from 5 to 60 mg, preferably from 10 to 40 mg, of β-adrenergic-blocking agent. This reduction exposes a person to far less risk of an adverse drug reaction.

It is important to insure the prompt entry of the β-adrenergic-blocking agent into the bloodstream. For this reason, the blocking agent may be provided in injectable form and administered parenterally. Another means of achieving prompt, effective bioavailability is by systemic administration of the blocking agent. A preferred systemic technique of nasal administration is described in, for example, U.S. Pat. Nos. 4,394,390 and 4,428,883 of Anwar A. Hussain et al, the disclosures of which are incorporated herein by reference.

In accordance with the foregoing, preferred dosage forms of the present invention comprise a β-adrenergic-blocking agent in a pharmaceutically acceptable nasal carrier. Any of the blocking agents can be conveniently administered in such a carrier. These compositions comprise a systemic, therapeutically effective amount of the desired drug together with a pharmaceutically acceptable nasal carrier.

Nasal carriers suitable in accordance with the present invention will be apparent to those skilled in the art of nasal pharmaceutical formulations. Exemplary nasal carriers include water, saline solutions; glycols such as propylene glycol; glycol ethers such as polyethylene glycol and combinations of the foregoing with water and/or one another. For still other examples, reference is made to the text entitled "REMINGTON'S PHARMACEUTICAL SCIENCES", 14th edition, 1970.

The choice of a suitable carrier in accordance with the present invention will depend on the exact nature of the particular nasal dosage form required. A therapeutic agent may, for example, be formulated into a nasal solution (for use as drops or as a spray), a nasal suspension, a nasal ointment, a nasal gel or any other nasal form. Preferred nasal dosage forms are solutions, suspensions or gels. These normally contain a major amount of water (preferably purified water) in addition to the active ingredient. Desirably, these compositions comprise at least 60% water by total weight.

Minor amounts of other ingredients such as tonicity agents (e.g. NaCl), pH adjusters (e.g., a base such as NaOH, acids such as citric), emulsifiers or dispersing agents, buffering agents, preservatives, wetting agents, thickening agents (e.g. polyvinyl alcohol) and gelling agents (e.g. polaxamer) may also be present. Particularly preferred compositions contain sufficient amounts of the foregoing and/or other ingredients to be a substantially isotonic and/or buffered to a physiologically acceptable pH.

As previously discussed, the efficacy of a β-adrenergic-blocking agent is dependent upon its presence at the desired site of drug activity. This is commonly reflected by its concentration in the blood of the subject being treated. It is therefore particularly significant that the present nasal administration of β-adrenergic-blocking agent is characterized by a virtually instantaneous and pronounced blood concentration as compared to conventional procedures of oral administration.

To maximise its efficacy, it is desirable that the presence of β-adrenergic-blocking agent in a therapeutically effective amount be maintained over a substantial period of time. Thus it is preferred to sustain an appropriate blood concentration of blocking agent for at least two hours after onset of aura. This may be ensured by repeating the initial administration, usually at least twice, over spaced intervals during this or any longer time period selected.

Those skilled in the art will be aware that a therapeutically effective amount of a particular β-adrenergic-blocking agent will vary with the particular drug as well as the type, age, size, weight and general physical condition of the subject. The amount will also vary dependent upon the particular therapeutic effect desired. Typically, however, the present dosage will be significantly less than that currently employed for analogous prophylactic treatment.

Any of the β-adrenergic-blocking agents known in the art may be utilized in accordance with the present invention. This includes blocking agents in their basic states or as their acid addition salts. Certain β-adrenergic-blocking agents are, however, preferred. These include propranolol, nadolol, timolol, metoprolol, atenolol, labetolol, pindolol, oxprenolol and their salts. Of these, timolol and especially propranolol (or their salts) are particularly preferred.

In formulation of the present compositions, a relatively water soluble form of β-adrenergic-blocking agent is usually employed. Use of a fully dissolved or solubilized blocking agent maximizes its immediate effect. This insures an essentially immediate, elevated effect. A partly soluble and delayed release form may also be included to assist in maintaining a therapeutically effective amount of blocking agent for the reason previously discussed.

The following is given by way of illustration only and is not to be considered limitative of this invention. Many apparent variations are possible without departing from the spirit and scope thereof.

EXAMPLE

A panel of individuals who were subject to frequent and severe migraine headache attacks were randomly divided into two groups to perform a double blind study. One group was designated to receive a placebo; the other, an active solution containing 50 mg of propranolol hydrochloride per milliliter of aqueous carrier.

Both groups of individuals were instructed to commence using sprays of their assigned study medications as seen as the aura of a migraine attack was sensed. Two 0.1 ml sprays were administered at time zero, followed by single 0.1 ml sprays in half-hour increments at ½, 1, 1½, and 2 hours from onset of the aura. This provided individuals in the group receiving active medication with a maximum total dosage of 30 mg of propranolol per person.

During the treatment, each person in the two groups evaluated the relative severity of headache symptoms for the categories of nausea, photosensitivity and pain. Data from a series of two headaches per person was then correlated to the scores for these categories at the time of onset of the migraine headache.

In correlating this data, the average scores of each group for nausea, photosensitivity and pain at aura were subtracted from the respective scores at each time of assessment. This provided a normalized measure of the relative effects of the two kinds of sprays. Increases over the baseline symptoms at aura were assigned positive values; decreases (or recovery/improvement), negative values.

Figure 2:
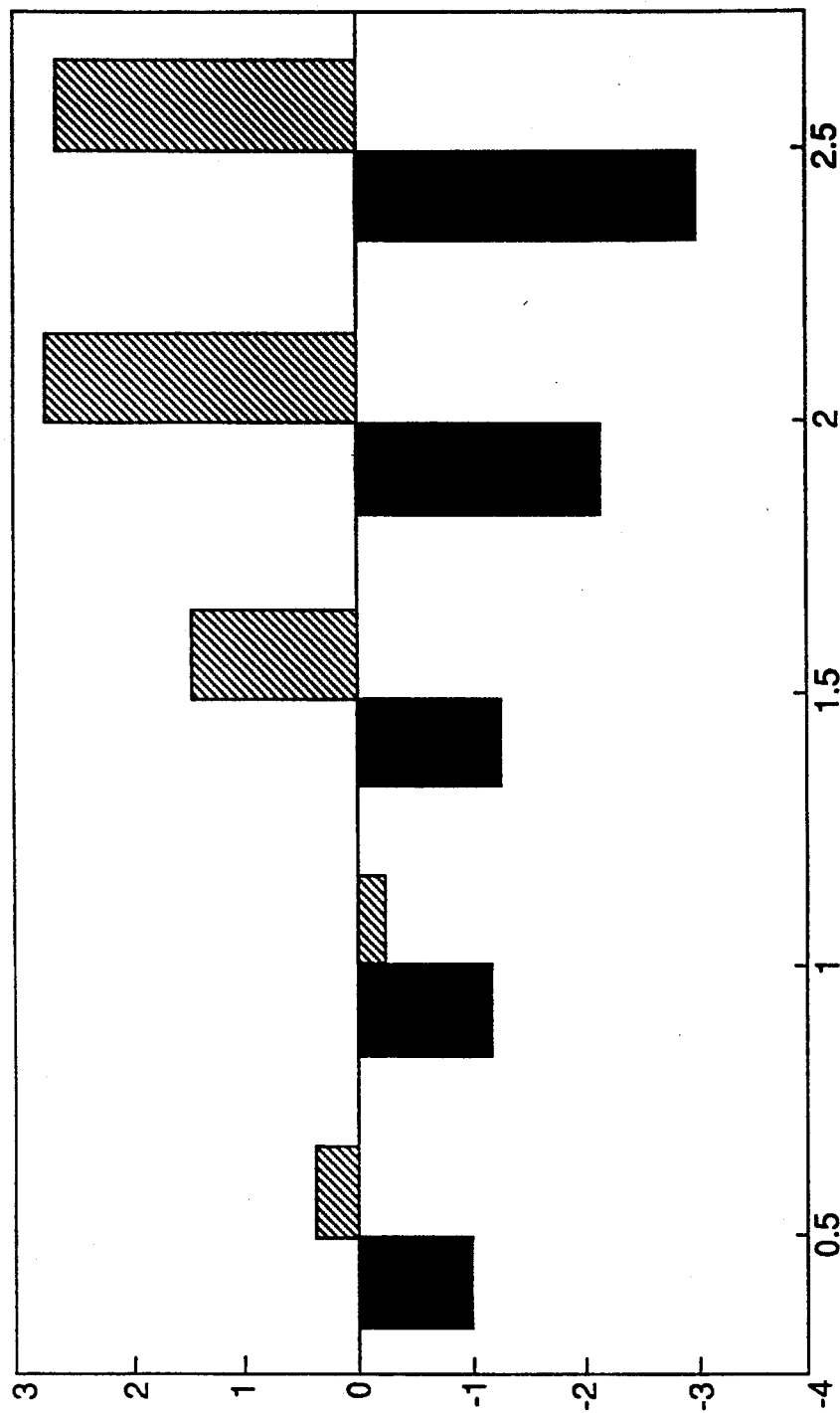
FIG. 2 is a graphic depiction of the comparative results on photosensitivity experienced by individuals having migraines treated with β-adrenergic-blocking agent as opposed to placebo.
Figure 3:
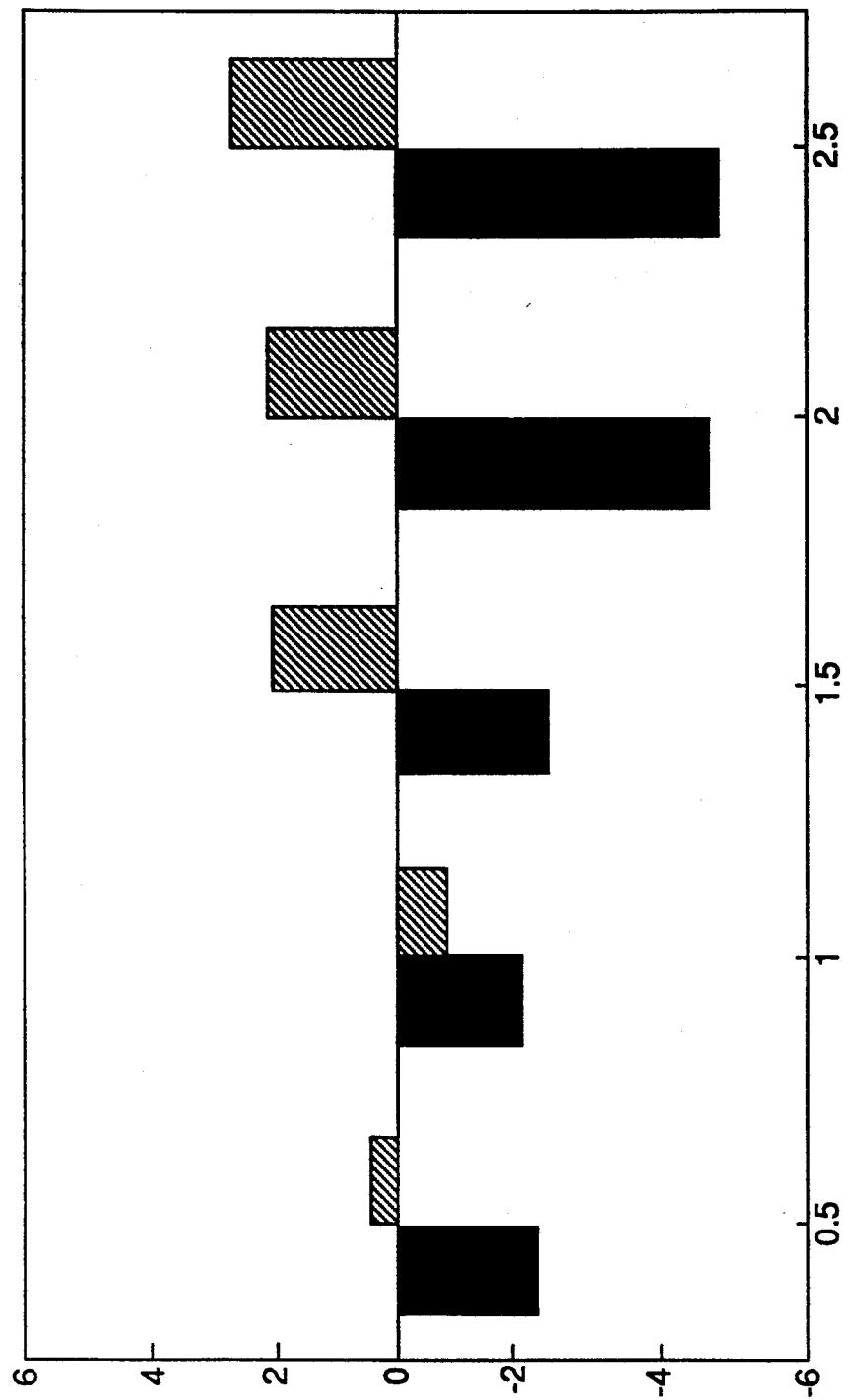
FIG. 3 is a graphic depiction of the comparative result on pain experienced by individuals having migraines treated with β-adrenergic-blocking agent as opposed to placebo.

The results from these calculations are graphically reflected in FIGS. 1–3. There, the lightly lined bars represent the test results for the placebo; the darkly solid bars, those for the propranolol. These results are graphed against time, measured in half hour increments from the time (0) of initial administration of spray. In each instance, the headache symptoms for the placebo group continued to worsen over time. In contrast, the individuals administered propranolol reported significant improvements in each of the categories of nausea, photosensitivity and pain.

These graphs clearly reflect that, contrary to prior belief, propranolol can be utilized in other than a prophylactic manner to control migraines. Where the propranolol is promptly administered after aura, the normal increases in the severity of symptoms are not only interrupted, but there is a significant recovery from the migraine attack. Thus, properly administered, such a β-adrenergic-blocking agent may be utilized to successfully treat these headache symptoms.

In further investigation of these surprising results, propranolol was administered to individuals on isolated days by three different routes. It was taken orally, through injection and nasally by spray. Each person's blood was assayed before and after each administration for propranolol concentration. The results of this investigation were then graphed in FIG. 4.

On this graph, the Y-axis reflects plasma propranolol concentration in nanograms per milliliter (ng/ml); the X-axis, time in hours after dosage. Plot points for the different routes of administration are designated respectively as: oral, squares and triangles; injection, plus signs; and nasal, circles. The oral dosages were performed by way of a tablet containing either 20 or 80 mg, respectively, while the injection and nasal dosages were each 5 mg of propranolol.

Figure 4:
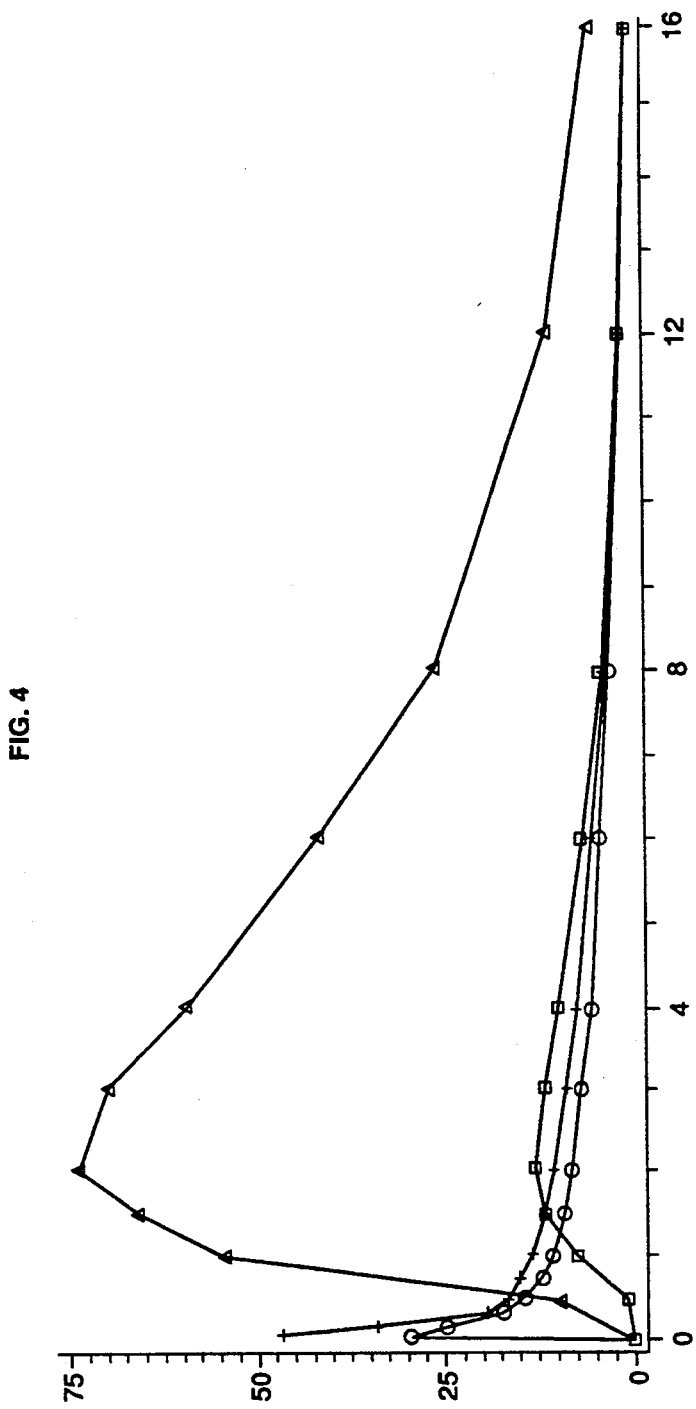
FIG. 4 is a graph of plasma concentration, measured as a function of time, of β-adrenergic-blocking agent administered pursuant to different means.

As shown by FIG. 4, a maximum blood level concentration of propranolol is reached almost immediately by either injection or nasal administration. In both instances, these concentrations reach about 47 ng/ml (injection) and 32 ng/ml (nasal) within five minutes.

After oral administration, on the other hand, the plasma concentration of propranolol increases much more slowly. Even as a dosage rate of 80 mg, sixteen times that employed for injection or nasal administration, as much as an hour is required before a comparable concentration is obtained through an oral dosage. At an oral dosage rate of 20 mg, the peak concentration is reached in two hours and obtains only a fraction of that achieved by the injection or nasal routes for their much smaller doses. Thus, only through much faster means than oral administration can a person act to achieve a therapeutically effective amount of drug promptly after onset of a migraine attack.

Figure 5:
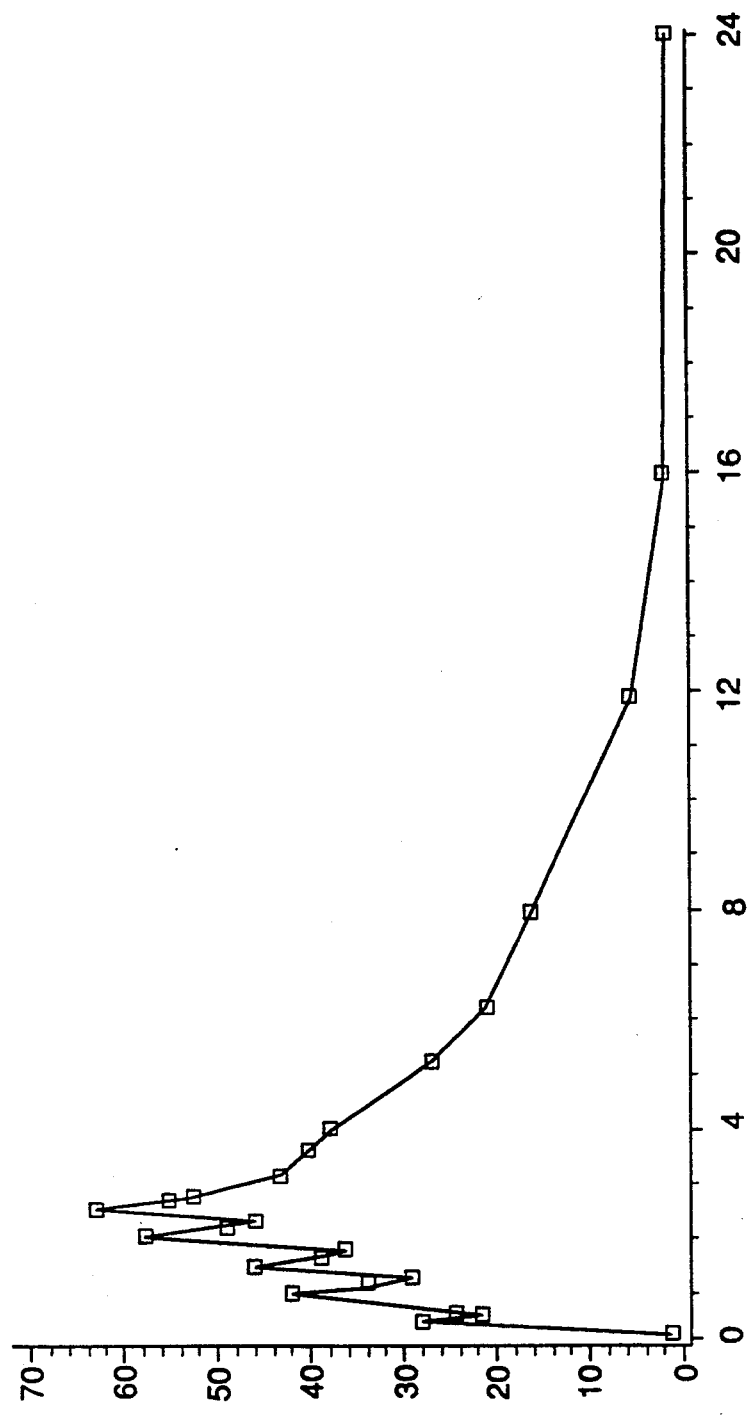
FIG. 5 is a graph of the plasma concentration of β-adrenergic-blocking agent pursuant to a series of nasal administrations.

The results of a still further investigation are graphed in FIG. 5. On this graph, the axes are as previously described. The plot points were obtained in the manner previously described for nasal administration, except that after an initial 10 mg of propranolol, dosing was repeated four more times at half hour intervals with additional 5 mg sprays of propranolol.

As shown by FIG. 5, where there is a properly spaced series of nasal administrations of propranolol, a high plasma concentration of propranolol can be maintained (or, as here, actually increased incident each repeat dosage) over a substantial period of time. Through comparison with the curves of FIG. 4, it may be seen that this embodiment of the present invention preserves the desired objective of an almost immediate, therapeutic concentration of drug while further establishing a maintenance level which approaches that achieved by an oral dosage. Moreover, it does so utilizing only a fraction of the total amount of propranolol necessary for an equivalent oral administration.

These investigations suggest that past failures to appreciate that β-adrenergic-blocking agent could be effective for more than prophylaxis of migraine may have resulted from a combination of factors. Firstly, the prior art does not appear to recognize the necessity of providing a therapeutically effective amount of blocking agent promptly after a classic migraine attack begins. Secondly, its reliance on conventional, oral routes of administration would have practically precluded achieving this objective (as reflected, for example, by its concentration in the blood) within the short time necessary for effective treatment of the attack.

While this invention has been described and illustrated with reference to certain preferred embodiments thereof, those skilled in the art will appreciate that various changes, modifications and substitutions can be made therein without departing from the spirit of the invention. Such expected differences in the practice of the present invention and the results obtained are contemplated in accordance with the objects and practices of the present invention. It is intended, therefore, that the invention be limited only by the scope of the claims which follow.

What is claimed is:

1. A method for treatment of a person suffering a classic migraine attack comprising administering a β-adrenergic-blocking agent to said person to provide a therapeutically effective amount of said blocking agent promptly after the onset of aura.

2. The method of claim 1, wherein the blocking agent is selected from the group consisting of propranolol, nadolol, timolol, metoprolol, atenolol, labetolol, pindolol, oxprenolol and a salt thereof.

3. The method of claim 2, wherein the administration commences within ten minutes of onset of aura.

4. The method of claim 3, wherein administration occurs nasally and is repeated at least twice over spaced intervals during a two hour time period following the initial administration of the blocking agent.

5. The method of claim 4, wherein the blocking agent comprises propranolol or a salt thereof.

6. The method of claim 1, wherein the blocking agent is systemically administered.

7. The method of claim 6, wherein the blocking agent is administered in a nontoxic pharmaceutically acceptable nasal carrier.

8. The method of claim 7, wherein the agent is administered in a composition selected from the group consisting of solution, suspension, ointment and gel.

9. The method of claim 8, wherein the carrier comprises at least 60 percent water by total weight.

10. The method of claim 9, wherein the composition is substantially isotonic and buffered to the pH of blood serum.

11. The method of claim 10, wherein the blocking agent in the composition is substantially completely solubilized.

12. The method of claim 11, wherein the blocking agent administered comprises from 5 to 60 mg of propranolol or a salt thereof.

13. The method of claim 12, wherein nasal administration is repeated at least twice over spaced intervals during a two hour time period following the initial administration of the blocking agent.

14. The method of claim 1, wherein the therapeutically effective amount of blocking agent is maintained for at least 2 hours after onset of aura.

15. The method of claim 14, wherein the blocking agent is nasally administered.

16. The method of claim 15, wherein nasal administration is repeated at least twice over spaced intervals during a two hour time period following the initial administration of the blocking agent.

17. The method of claim 16, wherein the composition administered comprises from 5 to 60 mg of a blocking agent selected from the group consisting of propranolol, nadolol, timolol, metoprolol, atenolol, labetolol, pindolol, oxprenolol and a salt thereof.

* * * * *